United States Patent [19]

Schneider et al.

[11] 4,275,254
[45] Jun. 23, 1981

[54] DIMERIZATION OF NORBORNADIENE TO A MIXTURE OF EXO-ENDO AND ENDO-ENDO HEXACYCLIC DIMERS

[75] Inventors: Abraham Schneider, Overbrook Hills; Harry K. Myers, Jr., Aston; George Suld, Springfield, all of Pa.

[73] Assignee: Suntech, Inc., St. Davids, Pa.

[21] Appl. No.: 639,742

[22] Filed: Dec. 11, 1975

[51] Int. Cl.$^3$ .................................. C10L 1/04
[52] U.S. Cl. ............................. 585/14; 60/211; 60/215; 585/360
[58] Field of Search .................. 60/211, 215; 260/666 PY; 44/80; 585/14, 360

[56] References Cited

U.S. PATENT DOCUMENTS

| | | | |
|---|---|---|---|
| 3,113,421 | 12/1963 | Koch | 60/211 X |
| 3,113,426 | 12/1963 | Smith et al. | 60/211 X |
| 3,165,887 | 1/1965 | Koch | 60/211 X |
| 3,242,667 | 3/1966 | Kidwell | 60/215 |
| 3,703,361 | 11/1972 | Konecky | 60/215 X |

Primary Examiner—Leland A. Sebastian
Attorney, Agent, or Firm—J. Edward Hess; Donald R. Johnson; Anthony Potts, Jr.

[57] ABSTRACT

Norbornadiene [bicyclo (2.2.1) heptadiene-2,5] is dimerized to a mixture of mainly the exo-endo stereoisomer of the hexacylic dimer of norbornadiene at both an excellent selectivity and conversion using an effective amount of a two component catalytic system of rhodium acetylacetonate and diethylaluminum chloride or ethylaluminum dichloride or aluminum ethylsesquichloride. The mixture also contains the endo-endo stereoisomer and some trimer. After hydrogenation a suitable mixture of the exo-endo and endo-endo dimers can be used as a component of high energy fuel.

11 Claims, 1 Drawing Figure

THEORETICALLY POSSIBLE DIMERS OF NORBORNADIENE

PENTA-CYCLICS exo-t-exo    endo-t-endo    exo-t-endo    exo-c-exo    endo-c-endo    exo-c-endo

HEXA-CYCLICS endo-endo    exo-exo    exo-endo    endo-exo

HEPTA-CYCLICS

Binor-S

THEORETICALLY POSSIBLE DIMERS OF NORBORNADIENE
PENTA-CYCLICS: exo-t-exo, endo-t-endo, exo-t-endo, exo-c-exo, endo-c-endo, exo-c-endo
HEXA-CYCLICS: endo-endo, exo-exo, exo-endo, endo-exo
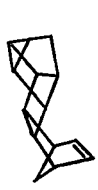
HEPTA-CYCLICS: Binor-S, exo-exo, exo-endo, endo-exo
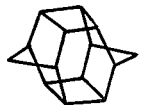
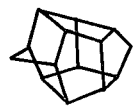

DIMERIZATION OF NORBORNADIENE TO A MIXTURE OF EXO-ENDO AND ENDO-ENDO HEXACYCLIC DIMERS

The invention herein described was made in the course of or under a contract thereunder with the United States Air Force Systems Command.

CROSS REFERENCES TO RELATED APPLICATIONS

This application is related to applicants' U.S. patent application Ser. No. 640,102 filed same date. The subject matter of the latter is directed to a method for making the endo-endo stereoisomer of the hexacyclic dimer of norbornadiene.

BACKGROUND OF THE INVENTION

This invention generally relates to mixtures resulting from the dimerization of norbornadiene. In particular, the invention relates to a mixture having a high concentration of a monoolefinic hexacyclic hydrocarbon known by the systematic chemical name of exo-endo stereoisomer of hexacyclo $(7.2.1.0^{2,8}.1^{3,7}.1^{5,13}.1^{4,6})$tetradec-10-ene (also designated as hexacyclo $[9.2.1.0^{2,10}.0^{3,8}.0^{4,6}.0^{5,9}]$tetradec-12-ene). The stereoisomer results from the catalytic dimerization of norbornadiene which is a $C_7H_8$ bicyclic, diolefinic hydrocarbon. More particularly, the invention relates to a mixture containing a high concentration of the exo-endo form of the hexacyclic dimer of norbornadiene and some endo-endo hexacyclic dimer of norbornadiene. Both of the dimers are $C_{14}H_{16}$, six-ring monoolefinic hydrocarbons. Also, the invention relates to a mixture of the foregoing which has been hydrogenated to convert the monoolefinic hexacyclic hydrocarbon to a completely saturated hexacyclic hydrocarbon. Hydrogenation of a monoolefinic hexacyclic dimer to the saturated dimer improves stability of the product towards oxidation thereby enhancing its utility as a high energy fuel. A mixture of completely saturated exo-endo and endo-endo hexacyclic dimers has a utility as a component of a high energy fuel.

An object of present invention is to provide a composition which has a maximum concentration of hexacyclic norbornadiene dimers and a minimal concentration of pentacyclic norbornadiene dimers and other compounds. Also the composition can be used as a component of high energy fuel for use in either jet or rocket propulsion. Jet propulsion includes a jet engine which can be used for missile, plane and other applications and includes the three basic types, i.e., ramjet, turbo-jet and pulse jet. The term jet generally refers to a device requiring air whereas rocket generally refers to a device containing its own oxygen or oxidizing agent.

Another object of present invention is to provide a novel method for preparing the foregoing composition. Still another object is the dimerization of norbornadiene at both excellent selectivity and conversion to the exo-endo form of the four possible stereoisomeric hexacyclic dimers.

Norbornadiene is also known as bicyclo-[2.2.1] heptadiene-2,5. A method of preparation is disclosed in U.S. Pat. No. 2,875,256, issued Feb. 24, 1959. Norbornadiene will be referred to as NBD hereinafter. NBD can be represented by either one of the following structural foamulas:

 or 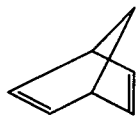

Dimerization of NBD is disclosed in U.S. Pat. No. 3,377,398, issued Apr. 9, 1968. The disclosed process results in the production of various dimer mixtures. The process therein involves the use of an iron catalyst system, e.g., ferric acetylacetonate and triethylaluminum, and a temperature above 140° C. The product of said method is a mixture which includes both monoolefinic hexacyclic and diolefinic pentacyclic dimers.

U.S. Pat. No. 3,282,663, issued Nov. 1, 1966, also discloses the dimerization of NBD to pentacyclic and hexacyclic dimers. In one example, ferric acetylacetonate and triethylaluminum is the catalyst. One of the dimers reported therein, i.e., Dimer III, has been identified as the endo-endo stereoisomer of the hexacyclic dimer of norbornadiene.

U.S. Pat. No. 3,326,992, issued June 20, 1967, discloses the partial hydrogenation of NBD dimer mixtures.

German patent publications Nos. 215332 and 2153314 disclose catalytic complexes of rhodium and iridium. Publication date for both of the aforementioned publications is Apr. 27, 1972. Both are West German publications.

A catalytic reaction between NBD and butadiene is disclosed in an article in the Journal of Organic Chemistry, Jan., 1970, Vol. 35, title, "Catalytic Norbornadiene-Butadiene and Norbornadiene-1,1-Dimethylallene Codimerization", by A. Greco et al., pages 271–274. One of the disclosed catalysts is a three component system of tris(acetylacetonate)iron-AlEt$_2$Cl-bis (diphenylophosphine)ethane. AlEt$_2$Cl refers to diethylaluminum chloride. One of the dimers reported therein, i.e. FIG. 1e, has been identified as the exo-exo stereoisomer of the hexacyclic dimer of norbornadiene.

Also, a catalytic reaction of NBD is disclosed in an article in The Journal of the American Chemical Society, Vol. 94, July 26, 1972, starting page 5446, titled "Dimerization and Trimerization of Norbornadiene by Soluble Rhodium Catalyst", by Nancy Acton et al. Rhodium catalysts, such as [(C$_6$H$_5$)$_3$P]$_3$RhCl, are disclosed. NBD dimers disclosed include the exo-endo and endo-endo isomeric forms.

Another article, "Catalysis of Cycloaddition Reaction by Rhodium on Carbon", by J. J. Mrowca et al, Journal of the American Chemical Society, 88:17, Sept. 5, 1966, pages 4012–4015, discloses the use of rhodium on carbon to dimerize NBD. The resulting products contain a major amount of the exo-endo stereoisomer of the hexacyclic dimer of NBD and a minor amount of the endo-endo dimer.

As the previous discussion indicates, more than one NBD dimer is possible. G. N. Schzauzer, in his review "On Transition Metal-Catalyzed Reactions of Norbornadiene and the Concept of a Complex Multicenter Processes" in Advances on Catalysis 18, 373 (1968) Acad. Press, describes the fourteen theoretically possible dimers of NBD. The possible dimers, grouped according to the number of their carbocyclic rings, are shown in accompanying drawing. Any and each of the dimers shown in the drawing have different physical and chemical properties.

Thus, a specific synthesis problem in the dimerization of NBD, as can be visualized from the number of possible isomers, is to obtain both excellent selectivity and conversion to a desired isomer.

The advantages of the present invention are as follows. The production of exo-endo and endo-endo hexacyclic dimers are favored while the production of pentacyclics is minimized. The latter are not desirable as high energy fuels or components thereof because of their high melting points and separation of pentacyclic dimers from the hexacyclic dimers is commercially not feasible. On the other hand, a mixture of exo-endo and endo-endo hexacyclic dimers can be readily separated from small amounts of unreacted feed and other products, particularly higher boiling polymers such as trimers. Thus, a finished product can be obtained consisting essentially of the exo-endo and endo-endo material. Hydrogenation of the foregoing material provides a mixture which can be used as a component for high energy, high density fuel.

SUMMARY OF THE INVENTION

NBD is readily dimerized to the exo-endo form of the $C_{14}H_{16}$ hexacyclic dimer at both excellent selectivity and conversion with the endo-endo form of dimer as a minor coproduct. The dimerization requires an effective amount of a two component catalytic system of rhodium acetylacetonate and diethylaluminum chloride or ethylaluminum dichloride or aluminum ethylsesquichloride. The components are referred to hereinafter as $RhA_3$, DEAC, EADC and EASC respectively. Range of favorable temperatures is specified.

DESCRIPTION OF THE DRAWING

The accompanying drawing discloses the structure for the theoretically possible dimers of NBD. The dimers are grouped according to the number of their rings. Also shown, when applicable, are the isomeric prefixes.

DESCRIPTION

The catalytic dimerization of NBD via present invention can be represented by the following formula reaction:

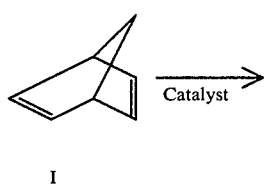

(A)

I
$C_7H_8$

-continued

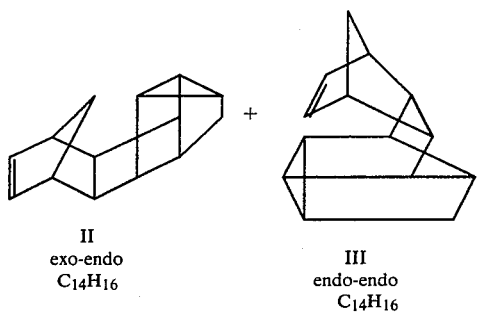

II
exo-endo
$C_{14}H_{16}$

III
endo-endo
$C_{14}H_{16}$

Compound I is NBD while compound II is the $C_{14}H_{16}$ hexacyclic exo-endo dimer of NBD and compound III is the endo-endo isomer.

Compound II is a major product whereas compound II is a minor coproduct. The word product as used herein refers only to compounds formed as a result of the dimerization reaction A; it does not include unreacted feed. Also the product may contain small amounts of other compounds such as pentacyclic dimers of NBD. However, the amount of pentacyclic dimers is nominal so it does not adversely effect the desired properties of the mixture. Any unreacted NBD, catalyst and smaller amount of heavier compounds can be separated from the product by distillation. An alternative procedure is that the catalyst can be deactivated by the addition of a hydroxylic solvent, e.g., methanol. This results in formation of two distinct layers which can be separated and then compounds II and III can be distilled from other hydrocarbons, if necessary.

Generally, the product contains a major amount of the exo-endo stereoisomer of NBD dimer and a minor amount of the endo-endo form of the dimer. Under more favorable conditions the product contains at least about 60 mole% and more typically at least about 70 mole% of the exo-endo stereoisomer form of the hexacyclic dimer of NBD. Furthermore, the amount of exo-endo stereoisomer present can be between from about 65 to about 90 mole %. Some of the balance of the product at the aforementioned levels is the endo-endo stereoisomer of hexacyclic dimer of NBD and the remaining balance is a trimer. Thus, at the higher levels of exo-endo stereoisomer the amount of endo-endo stereoisomer can range from between about 20 to about 5 mole %. The other coproduct, i.e., the trimer, may be present in an amount of from about 5 to about 20 mole %.

The catalytic system favoring the aforementioned dimerization reaction A contains two components. The two are $RhA_3$ and DEAC or EADC or EASC. The amount of the system present is an effective amount so that a suitable conversion to dimer occurs and the selectivity as to compounds II and III is sufficient. Any material which during the dimerization reaction could adversely effect the catalytic system should not be present. For example, the presence of hydroxylic compounds such as water, alcohol or oxygen from air could deactivate the catalyst system.

Selectivity refers to the amount of a particular compound formed divided by the amount of all compounds formed. Conversion to the dimer is the amount of total dimer formed divided by the sum of the total dimer plus unreacted feed. From a commercial standpoint economics of an overall process determines the optimal levels for both the selectivity and conversion.

The reaction time required for an economically satisfactory selectivity and/or conversion depends on a number of factors such as catalyst to NBD ratio as well as operating conditions. Also the economics depend on capital investment versus conversion per pass and the like. The catalyst to NBD ratios are discussed hereinafter while typical conditions are provided by the Examples.

The amount of $RhA_3$ present compared to NBD feed should be sufficient to obtain the desired product. Generally, the mole ratio of NBD to $RhA_3$ will range between from about 50/1 to about 5000/1 with a more typical range between from about 100/1 to about 2500/1.

DEAC or EADC or EASC is the second component of the catalytic system with EADC preferred. The amount of the second component can vary substantially but generally it relates to the amount of $RhA_3$ used. An effective mole ratio range of DEAC or EADC or EASC to $RhA_3$ can be between from about 0.5 to about 100 with about 2 to about 50 preferred and about 5 to about 20 more preferred. Excess DEAC or EADC or EASC also serves as a scavenger for any water and/or oxygen in the system. Generally, however, when DEAC or EADC or EASC is used it is advantageous to conduct the reaction under substantially anhydrous conditions and under an inert gas blanket.

A suitable solvent can be used in the dimerization reaction. Since the reaction is exothermic a solvent may serve as a heat sink. It can also assist in solubilizing the reaction components, that is the feed, and the components of the catalytic system and thereby provide for a homogeneous reaction medium. As stated previously, the solvent should not adversely react with the feed, products or catalyst. Also, presence of a solvent facilitates the handling of the reaction mixture. Classes of suitable solvents include aromatic hydrocarbons, cycloparaffins, halogenated aromatics, halogenated paraffins and halogenated cycloparaffins. Specific examples include benzene, toluene, xylenes, cyclohexane, chlorobenzene, bromobenzene, chlorinated cyclohexane and the like. As to the amount of solvent used, excessive amounts decrease the reaction rate, and thus adversely effect the economics for a commercial operation.

Selective dimerization of NBD occurs in the liquid phase therefore it is not desirable to have the reaction temperature largely exceed the boiling points of the NBD or solvent. Conversely, if the temperature is too low the reaction rate would be too low to be economically feasible. An operable temperature range is between from about 0° C. to about 200° C., with about 50° C. to about 100° C. a preferred range. Lower operating temperatures can reduce manufacturing costs because of less heat requirements.

The operating pressure can vary substantially, however, it can range from about atmospheric to up to about 2000 psi with 1000 a preferred upper value. Process economics favor lower operating pressure; however, a moderately elevated reaction pressure may be desirable to keep gaseous reaction components in solution.

The selective NBD dimerization of the present invention can be carried out in either a batch or a continuous process.

The product resulting from the aforementioned dimerization reaction A can be hydrogenated using a hydrogenation catalyst such as $PtO_2$ (Adams catalyst). The product generally would be hydrogenated after separation from the dimerization catalyst. The purpose of the catalytic hydrogenation is to saturate the olefinic bond of the hexacyclic stereoisomers of the NBD dimer and in particular, any olefinic bonds contained in the product. In general, compounds with olefinic bonds are not desirable in fuels, in part, because of their tendency to form gums and like materials, which can adversely effect the working of mechanical parts. Other problems also can be caused by compounds with olefinic bonds. Thus, the degree of hydrogenation should be sufficient to prevent the aforementioned problems. Furthermore, the length of time the product is stored influences the desired degree of necessary hydrogenation. In addition, certain additives, such as oxidation inhibitors, can be used to supplement the effect of hydrogenation. Generally, however, the degree of saturation is such that the monoolefinic hexacyclic NBD dimers are essentially completely converted to saturated hexacyclic hydrocarbons. It is preferred that the extent of hydrogenation be such that the conversion is complete as is determined by the infra-red technique.

To further illustrate the invention, the following examples are provided along with two comparative examples.

EXAMPLES

The accompanying Table I summarizes the dimerization runs which were carried out in 50 milliliter vessels closed with wired serum caps fitted with an internal immersion thermometer. The procedure was as follows. First the tubes were flushed with argon. Then the materials were added to the tubes in the following order; $RhA_3$, solvent, NBD (99% pure) and DEAC or EADC all at room temperature. This sequence was satisfactory and it is believed that other sequences will work equally well. Prior to use, the NBD (Aldrich, 99% pure) was percolated through alumina.

The test tubes were heated in an oil bath with temperatures as indicated in the Table I. The conversions and selectivities reported in Table I are based on analyses performed by vapor phase chromatography on both packed and capillary columns.

TABLE I

| | | | Dimerization of NBD** | | | | | |
|---|---|---|---|---|---|---|---|---|
| | | | Other Cat. Component | | | % Selectivity | | |
| Run | Time Min. | Amount* of $RhA_3$ | Type | Amount* | % Conversion | Exo-Endo | Endo-Endo | Trimer |
| 1 (a) | 60 | 0.06 | DEAC | 0.6 | 93.2 | *** | *** | *** |
| (b) | 120 | 0.06 | DEAC | 0.6 | 97.0 | 66.5 | 11.9 | 18.6 |
| 2 | 20 | 0.06 | EADC | 0.6 | 97.6 | 75.5 | 13.2 | 8.9 |

*millimoles
**temperature was about 70-80° C.; 30 millimoles of NBD and 1 milliliter of solvent were used.
***not analyzed.

High conversions were obtained using the catalyst system of the present invention. Runs 1 and 2 demonstrate this with conversions of about 97%. Run 2 with a conversion of 97.6% after 20 minutes further indicated a rapid conversion.

In both runs 1 and 2 selectivities as to the exo-endo stereoisomer of NBD dimer were in excess of 65%. Selectivities as to the total of exo-endo and endo-endo of said dimer were 78.4% and 88.7% for runs 1 and 2 respectively. Such high selectivities indicate the presence of only minor amounts of other volatile coproducts such as trimer.

A sample of the product from the foregoing runs was hydrogenated in a 500 milliliter Parr glass reactor charged with $PtO_2$ (Adams catalyst). Hydrogen was fed to the reactor while it was agitated by shaking. The temperature was ambient. After sufficient time the addition of hydrogen was stopped and the mixture removed from the reactor. The catalyst was then separated from the liquid concentrate. A sample of the hydrogenated dimer showed no residual double bonds by infra-red. In addition, vapor phase chromatography was used to follow the hydrogenation progress.

A mixture containing 85.5% of the saturated exo-endo hexacyclic dimer of NBD, 11.6% of the saturated endo-endo and 2.9% of saturated pentacyclic dimers of NBD, had a melting point of the last crystal of +45° F. After blending the latter with an equal amount of a mixture containing 71.1% of the saturated endo-endo hexacyclic dimer of NBD, 18.4% of the saturated exo-endo and 10.5% of the saturated pentacyclic dimers of NBD, the resulting 50–50 mixture had a melting point of its last crystal of −65° F.

The composition of the foregoing resulting mixture contained about 41.4% of saturated endo-endo hexacyclic dimer of NBD and 51.9% of saturated exo-endo hexacyclic dimer of NBD and 6.7% of saturated pentacyclic dimers of NBD. Thus, a composition having sufficient amounts of saturated exo-endo and endo-endo stereoisomers can have a melting point of its last crystal low enough to permit use of the composition as a high energy fuel. A preferred composition would contain an amount in between from about 40% to about 60 mole % of saturated endo endo stereoisomer and between from about 40% to about 60 mole % of the saturated exo-endo stereoisomer and minor amounts of saturated pentacyclic dimers of NBD. A preferred range of the melting point of the last crystal would be in the range between from about −10° F. to about −65° F.

It should be noted that the feed to the foregoing reaction A consists essentially of NBD. Thus, for example, additional reactive monoolefinic and diolefinic hydrocarbons should be excluded.

Use of EASC in place of DEAC or EADC in the aforementioned runs will yield analogous results.

Two comparative runs were made. In one run triisobutyl aluminum was used in place of DEAC or EADC and in another diisobutyl aluminum ethoxide($iBu_2AlOEt$) was used in place of DEAC or EADC. In both of these runs the conversions after 100–120 minutes were 2.3% and 1.0% respectively. Thus, these two materials were not satisfactory for obtaining high conversions in a reasonable amount of time.

We claim:

1. A process for dimerizing norbornadiene comprising:
   (a) contacting a feed consisting essentially of norbornadiene in the presence of an effective amount of a two-component catalytic system consisting of rhodium acetylacetonate and one of the following: diethylaluminum chloride, ethylaluminum dichloride and aluminum ethylsesquichloride;
   (b) said contacting occurring within a temperature range between from about 0° C. to about 200° C.; and whereby a major product is an exo-endo form of a hexacyclic dimer or norbornadiene and two coproducts are an endo-endo form of a hexacyclic dimer of norbornadiene and a trimer of norbornadiene.

2. Process according to claim 1 wherein the mole ratio of norbornadiene to rhodium acetylacetonate is between from about 50/1 to about 5000/1.

3. Process according to claim 1 wherein the mole ratio of diethylaluminum chloride or ethyl aluminum dichloride to rhodium acetylacetonate is between from about 0.5 to about 100.

4. Process according to claim 3 wherein the mole ratio of norbornadiene to rhodium acetylacetonate is between from about 50/1 to about 5000/1.

5. Process according to claim 4 wherein the product contains from about 65 to about 90 mole % of the exo-endo form of the hexacyclic dimer of norbornadiene and from about 20 to about 5 mole % of the endo-endo form of the hexacyclic dimer of norbornadiene and the balance is the trimer.

6. A composition consisting essentially of sufficient amounts of saturated exo-endo hexacyclic dimer of NBD and saturated endo-endo hexacyclic dimer of NBD wherein the composition has a melting point of its last crystal low enough to permit use of the composition as a high energy fuel.

7. Composition according to claim 6 wherein the amount of saturated exo-endo hexacyclic dimer of NBD is between from about 40% to about 60 mole %.

8. Composition according to claim 7 wherein the amount of saturated endo-endo hexacyclic dimer of NBD is between from about 40% to about 60 mole %.

9. Composition according to claim 8 containing a minor amount of saturated pentacyclic dimer.

10. Composition according to claim 6 wherein the melting point is between from about −10° F. to about −65° F.

11. Composition according to claim 9 wherein the melting point is between from about −10° F. to about −65° F.

* * * * *